United States Patent
Au et al.

(10) Patent No.: US 10,074,256 B2
(45) Date of Patent: Sep. 11, 2018

(54) DETECTION SYSTEM AND METHOD FEATURING MULTISPECTRAL IMAGING DEVICE

(71) Applicant: Honeywell International Inc., Morris Plains, NJ (US)

(72) Inventors: Kwong Wing Au, Bloomington, MN (US); Christopher Larsen, Rockford, MN (US)

(73) Assignee: Honeywell International Inc., Morristown, NJ (US)

(*) Notice: Subject to any disclaimer, the term of this patent is extended or adjusted under 35 U.S.C. 154(b) by 0 days.

(21) Appl. No.: 15/535,349

(22) PCT Filed: Dec. 10, 2015

(86) PCT No.: PCT/US2015/064887
§ 371 (c)(1),
(2) Date: Jun. 12, 2017

(87) PCT Pub. No.: WO2016/100063
PCT Pub. Date: Jun. 23, 2016

(65) Prior Publication Data
US 2017/0358190 A1   Dec. 14, 2017

Related U.S. Application Data

(60) Provisional application No. 62/093,257, filed on Dec. 17, 2014.

(51) Int. Cl.
*G01J 5/02* (2006.01)
*G08B 17/12* (2006.01)
*G01N 21/63* (2006.01)

(52) U.S. Cl.
CPC ............ *G08B 17/125* (2013.01); *G01N 21/63* (2013.01)

(58) Field of Classification Search
CPC ........ G01J 5/602; G01J 5/0014; G01J 3/0264; G01J 3/26; G08B 17/125; G01N 21/71
See application file for complete search history.

(56) References Cited

U.S. PATENT DOCUMENTS 5,677,532 A     10/1997  Duncan et al.
6,473,238 B1 *  10/2002  Daniell ................ G02B 3/005
                                              348/E13.028
(Continued)

FOREIGN PATENT DOCUMENTS

CN    101577033 A    11/2009
EP    1329860 A2     7/2003
(Continued)

OTHER PUBLICATIONS

PCT Application No. PCT/US2015/064887, International Search Report, dated Mar. 4, 2016, 4 pages.
(Continued)

*Primary Examiner* — Kiho Kim
(74) *Attorney, Agent, or Firm* — Wick Phillips Gould & Martin LLP

(57) ABSTRACT

Embodiments of the disclosure include systems and methods for detection of background and foreground radiances captured by a multispectral imaging device. In some embodiments, a multispectral imaging device may generate a plurality of images of the same field of view, wherein the images may be captured at a variety of wavelengths. These images may be processed to identify any incidents, such as fire and/or gas leaks, within the field of view of the imaging device.

20 Claims, 4 Drawing Sheets

(56) References Cited

U.S. PATENT DOCUMENTS

| | | | | |
|---|---|---|---|---|
| 7,679,046 | B1* | 3/2010 | Benson | H04N 5/33 250/252.1 |
| 8,300,890 | B1* | 10/2012 | Gaikwad | G06K 9/00771 382/103 |
| 2008/0266120 | A1* | 10/2008 | Leeland | F23N 5/02 340/578 |
| 2011/0169962 | A1* | 7/2011 | Gat | H04N 5/33 348/164 |

FOREIGN PATENT DOCUMENTS

| | | |
|---|---|---|
| JP | 2013036974 A | 2/2013 |
| WO | 2014179482 A1 | 11/2014 |
| WO | 2016100063 A1 | 6/2016 |

OTHER PUBLICATIONS

PCT Application No. PCT/US2015/064887, Written Opinion of the International Searching Authority, dated Mar. 4, 2016, 8 pages.
Gagnon, Marc Andre et al: "Time-resolved thermal infrared multispectral imaging of gases and minerals", Optomechatronic Micro/Nano Devices and Components III: Oct. 8-10, 2007, Lusanne Switzerland, vol. 9623, Nov. 18, 2014, pp. 1-10.
PCT Application No. PCT/US2015/064887, International Preliminary Report on Patentability, dated Jun. 20, 2017, 9 pages.

* cited by examiner

DETECTION SYSTEM AND METHOD FEATURING MULTISPECTRAL IMAGING DEVICE

CROSS-REFERENCE TO RELATED APPLICATIONS

The present application claims priority to and is the National Stage of International Application No. PCT/US2015/064887 (entitled "DETECTION SYSTEM AND METHOD FEATURING MULTISPECTRAL IMAGING DEVICE filed Dec. 10, 2015," which claims priority to U.S. Provisional Patent Application Ser. No. 62/093,257 (entitled DETECTION SYSTEM AND METHOD FEATURING MULTISPECTRAL IMAGING DEVICE filed Dec. 17, 2014)," both of which is incorporated herein by reference.

STATEMENT REGARDING FEDERALLY SPONSORED RESEARCH OR DEVELOPMENT

Not applicable.

REFERENCE TO A MICROFICHE APPENDIX

Not applicable.

BACKGROUND

Safety is a concern to industries where fire and gas leakage may result in loss of life, loss of production, and great liability. As such, it is common for owners and operators of building structures to rely on fire and gas detection systems for early detection and warning of fire, smoke and hazardous gas. These detection systems may alert supervisors and/or workers of a hazardous incident, allowing actions to be taken to dispel whatever incident is identified.

SUMMARY

Aspects of the disclosure may include embodiments of a system comprising a multispectral imaging device operable to capture images of a field of view at different wavelengths; and an electronic processing device coupled to the multispectral imaging device, wherein the processing device comprises a processor, a memory, and a user interface, and wherein the processing device is operable to save the multispectral images to the memory for access by the processor, separate background and foreground results from the multispectral images; evaluate the results for identification of an incident in the foreground region; and generate an alarm when the foreground region indicates a hazardous incident.

In some embodiments, the multispectral imaging device may comprise a microbolometer. In some embodiments, the electronic processing device is incorporated into the multispectral imaging device. In some embodiments, the multispectral imaging device comprises a filter wheel operable to filter different wavelengths as it rotates in front of a camera. In some embodiments, the multispectral imaging device comprises a lens array that is split into different wavelengths. In some embodiments, the multispectral imaging device comprises a plurality of cameras located within the multispectral imaging device. In some embodiments, the incident comprises a gas leak, wherein the specific gas type may be identified, and wherein the alarm is generated if the gas is identified to be a hazardous gas. In some embodiments, the incident comprises a fire. In some embodiments, the processing device is further operable to forward the processed images to a user interface for viewing.

Additional aspects of the disclosure may include embodiments of a method for detection of background and foreground radiances captured by a multispectral imaging device, the method comprising setting up a multispectral imaging system in a facility, wherein the field of view of the camera covers an area with the potential for a fire or gas incident; acquiring a plurality of spectral images from the multispectral imaging system; applying a calibration to each spectral image such that the intensity of a pixel is transformed to spectral radiance; applying one or more segmentation techniques to find regions in each spectral image; combining segmented regions from the spectral images to generate regions that have distinct spectral characteristics; estimating the background parameters of each pixel in each region based on spatial and spectral intensities; computing background spectral intensities based on the estimated background parameters; computing foreground spectral intensities by subtracting input intensity from the corresponding background intensity; and identifying an incident based on the computed foreground spectral intensities, wherein an incident is indicated by an increased or decreased foreground spectral intensity.

In some embodiments, the incident is identified when the computed foreground spectral intensities are higher or lower than predefined thresholds. In some embodiments, the method further comprises displaying the processed image(s) on a user interface. In some embodiments, estimation is based on averaging the background parameters computed using black body radiation assumptions based on multispectral pixel intensities. In some embodiments, neighborhood pixel intensities are used for better fit during estimation. In some embodiments, the background parameters include temperature and emissivity. In some embodiments, the method further comprises applying one or more noise removal techniques to reduce the impact of noise and computational inaccuracy.

Other aspects of the disclosure may include embodiments of a system comprising a multispectral imaging device operable to capture images of a field of view at different wavelengths; and an electronic processing device coupled to the multispectral imaging device, wherein the processing device comprises a processor, a memory, and a user interface, and wherein the processing device is operable to acquire a plurality of spectral images from the multispectral imaging device; apply a calibration to each spectral image such that the intensity of a pixel is transformed to spectral radiance; apply one or more segmentation techniques to find regions in each spectral image; combine segmented regions from the spectral images to generate regions that have distinct spectral characteristics; estimate the background parameters, including temperature and emissivity, of each pixel in each region based on spatial and spectral intensities; compute background spectral intensities based on the estimated background parameters; compute foreground spectral intensities by subtracting input intensity from the corresponding estimated background intensity; and identify an incident based on the computed foreground spectral intensities, wherein an incident is indicated by a change in foreground spectral intensity.

In some embodiments, the multispectral imaging device may comprise a microbolometer. In some embodiments, the incident is identified when the computed foreground spectral intensities are higher or lower than predefined thresholds. In some embodiments, the processing device is further operable to display the processed image(s) on a user interface. In some embodiments, the processing device is operable to apply one or more noise removal techniques to reduce the impact of noise and computational inaccuracy.

These and other features will be more clearly understood from the following detailed description taken in conjunction with the accompanying drawings and claims.

BRIEF DESCRIPTION OF THE DRAWINGS

For a more complete understanding of the present disclosure, reference is now made to the following brief description, taken in connection with the accompanying drawings and detailed description, wherein like reference numerals represent like parts.

DETAILED DESCRIPTION

Figure 1:
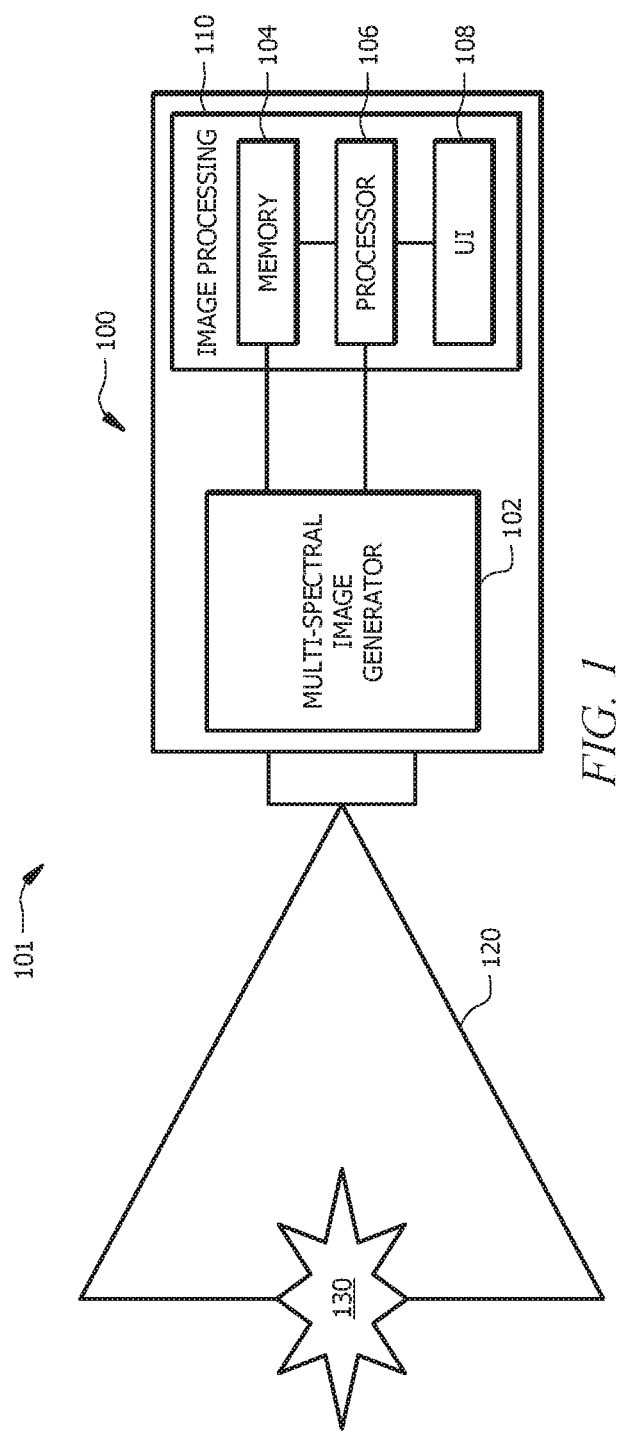
FIG. 1 illustrates a system including a multispectral imaging device according to an embodiment of the disclosure.

It should be understood at the outset that although illustrative implementations of one or more embodiments are illustrated below, the disclosed systems and methods may be implemented using any number of techniques, whether currently known or not yet in existence. The disclosure should in no way be limited to the illustrative implementations, drawings, and techniques illustrated below, but may be modified within the scope of the appended claims along with their full scope of equivalents.

The following brief definition of terms shall apply throughout the application:

The term "comprising" means including but not limited to, and should be interpreted in the manner it is typically used in the patent context;

The phrases "in one embodiment," "according to one embodiment," and the like generally mean that the particular feature, structure, or characteristic following the phrase may be included in at least one embodiment of the present invention, and may be included in more than one embodiment of the present invention (importantly, such phrases do not necessarily refer to the same embodiment);

If the specification describes something as "exemplary" or an "example," it should be understood that refers to a non-exclusive example;

The terms "about" or approximately" or the like, when used with a number, may mean that specific number, or alternatively, a range in proximity to the specific number, as understood by persons of skill in the art field; and If the specification states a component or feature "may," "can," "could," "should," "would," "preferably," "possibly," "typically," "optionally," "for example," "often," or "might" (or other such language) be included or have a characteristic, that particular component or feature is not required to be included or to have the characteristic. Such component or feature may be optionally included in some embodiments, or it may be excluded.

Embodiments of the disclosure include systems and methods for detection of background and foreground radiances captured by a multispectral imaging device. In some embodiments, a multispectral imaging device may generate a plurality of images of the same field of view, wherein the images may be captured at a variety of wavelengths. These images may be processed to identify any incidents, such as fire and/or gas leaks, within the field of view of the imaging device.

Safety is a major concern to industries where fire and gas leakage may result in major hazards that can result in loss of life, loss of production and great liability. As such, it is common for owners and operators of building structures to rely on fire and gas detection systems for early detection and warning of fire, smoke and hazardous gas.

Traditional detection systems typically require a large number of detectors in various areas throughout a building structure or facility. For example, acoustic sensors can be used to listen for gas leaks and numerous gas detectors can be deployed to sense the presence of specific gases. These sensors may be local, covering limited areas. Fire detectors based on triple Infrared (IR) sensors can also be deployed. Multiple redundant deployments to reduce false alarms are also common practice. However, overall cost of the fire and gas detection can become significant. More critically, the fire detector may not be able to pinpoint the exact location of the fire. Thus, a worker may have to be sent to confirm the presence of a fire, thus putting the worker in harm's way.

Recently, microbolometers (uncooled Infrared cameras) have become significantly more affordable. Generally, a microbolometer is capable of fire detection based on thermal radiation. In addition, adding a filter bank to a microbolometer may allow the microbolometer to detect radiations of selected spectral bands that can be used for detection of specific gas species. For example, a region of interest (e.g., a gas cloud) may be invisible in one wavelength (e.g., in green visible spectrum), but may be observed in another wavelength (e.g., in 4.3 medium wavelength IR (MWIR)). Thus, a multispectral imaging device may be useful for detecting a broad range of gasses. Consequently, devices and methods incorporating a multispectral microbolometer may be used to detect the presence of fire and hazardous gas and also provide a visual image and the location of the detection.

Each pixel of a multispectral image may represent the sum of signals from the background and foreground. For example, the background regions may be regions that belong to the scene, such as sky, man made and natural objects. The foreground regions may be regions of interest, such as fire, flame, gas cloud and smoke. In general, the foreground signal may be small compared to the background signal, making extraction of the foreground signal a daunting challenge. Thus, segmentation and detection of foreground from background regions are critical to detection.

Given a single-wavelength image of the scene, conventional background and foreground segmentation is typically based on subtraction of an estimated background image, which is commonly computed using a spatial filter. This approach works fairly well when the foreground signal is large. However, when the foreground signal is small, such as that of a gas cloud, true foregrounds may not be detectable or many generate false foregrounds. Thus, a more robust background and foreground segmentation is needed.

Embodiments presented herein may feature a low-cost multispectral imaging device such as a microbolometer for detection of fire and hazardous gas conditions. The microbolometer used in connection with such embodiments can be, for example, of a type similar to an ATOM 80—80×80 Uncooled Microbolometer Core as manufactured by Sofradir—EC, Inc. In some embodiments, the device may include a high sensitivity thermal imaging sensor/detector integrated with a filter wheel having neutral and multiple narrow band filters in front of the low cost microbolometer.

In some embodiments, the microbolometer may be used to capture a sequence of narrow-band IR images and an all-pass IR image which can be used in connection with spectral-based gas detection and radiation-based fire detection algorithms.

Referring now to FIG. 1, an embodiment of system 101 comprising a multispectral imaging device 100 is shown. In some embodiments, the multispectral imaging device 100 may comprise a microbolometer (as described above). In some embodiments, the multispectral imaging device 100 may comprise a multispectral image generator 102 and a processing device 110 operable to receive data from the multispectral image generator 102. In some embodiments, the processing device 110 may comprise a memory 104, a processor 106, and a user interface (UI) 108, wherein the elements may be operable to communicate information to one another. In some embodiments, the processing device 110 may be a part of the multispectral imaging device 100. In other embodiments, the processing device 110 may be separate from the multispectral imaging device 100, wherein the multispectral imaging device 100 may communicate information to the processing device 110.

In some embodiments, the multispectral imaging device 100 may be operable to communicate with a monitoring station or device, wherein the results of the processing of the images may be communicated to and displayed on the monitoring station. In some embodiments, the processing device 110 may be located remotely from the multispectral imaging device 100, and may be viewed by a monitor or supervisor.

In some embodiments, the multispectral image generator 102 may comprise a filter wheel operable to filter different wavelengths as it rotates in front of a camera. In some embodiments, the multispectral image generator 102 may comprise a lens array that is split into different wavelengths. In some embodiments, the multispectral image generator 102 may comprise a plurality of cameras located within the multispectral imaging device 100, wherein each camera may capture a different wavelength band.

Embodiments of the disclosure may include any of a plurality of methods for generating multispectral images, as would be understood by one skilled in the art. Regardless of the method for capturing the multispectral images, the multispectral image generator 102 may produce a plurality of images, each captured at a different wavelength, wherein the images show the same field of view 120. In some embodiments, the multispectral imaging device 100 may receive images of an incident 130 within the field of view 120 of the multispectral imaging device 100. The incident 130 may be a fire, a gas leak, or other similar incident.

In some embodiments, the processor 106 may receive the multispectral images and complete processing on the images, as described in further detail below. In some embodiments, the memory 104 may store the images generated by the multispectral image generator 102. In some embodiments, images may be generated at periodic time intervals. In some embodiments, the processed results may be displayed by the user interface 108.

Embodiments of the disclosure may perform a precise separation of background thermal radiation from the foreground thermal radiation. For example, the total radiance, $R_T$, sensed by each pixel of the microbolometer can be derived from the sum of background radiance, $R_B$, and foreground radiance, $R_F$, (i.e., $R_T=R_B+R_F$). Generally, the background radiance may come from the sky, natural vegetation, and man-made objects and can behave like black bodies or gray bodies. The foreground thermal radiation of interest can belong to that of a flame ($R_f$) and gases (or gas radiance) ($R_g$). However, these elements behave very differently. Accordingly, embodiments disclosed herein may treat them differently for their respective detections. For example, a fire generally burns at a temperature that is much higher than that of background radiance. As a result, the dominant radiance is the flame radiance, $R_f$.

Figure 2A:
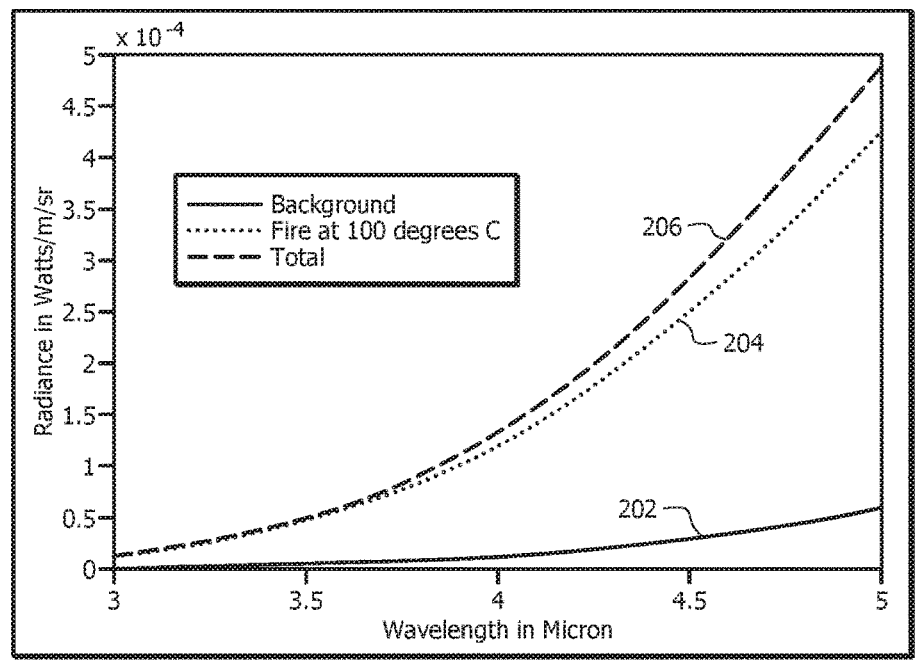
FIGS. 2A-2D illustrate graphs and charts illustrating elements of one or more embodiments of the disclosure.

FIG. 2A illustrates a background radiance at 25° C. (202), a fire radiance at 100° C. (204) and the total radiance (206). Segmentation of the fire radiance 204 from the background region 202 can be accomplished based on the thermal contrast between the two in the all-pass IR image. The challenge in fire detection is to avoid detection of other high temperature objects, such as sun, as fire also. On the other hand, the dominant radiance comes from the background in gas detection.

Embodiments presented herein can extract the foreground regions in each spectral image by subtracting an estimated background image from the corresponding spectral image. Such embodiments can further estimate the spectral background from the same regions of all spectral images. That is, the background estimation may be based on a combination of spatial and spectral information, unlike the conventional approach which uses only the spatial information.

A set of multi spectral images may consist of multiple images of the same scene (or field of view), each of which can correspond to the sensed intensities from a particular wavelength or a narrow band of wavelengths. As such, one location in a facility or building structure can be captured with pixels of different spectral wavelengths at the same image coordinate. As described below, the pixels can be fit into Planck's function of temperature and the resulting Planck's radiation at a predetermined temperature can become the estimated background. In addition, to reduce the impact of noise and other environmental influences, neighboring pixel locations can be included in Planck's function.

Once the best fitted Planck's function is estimated, the background signals can be identified as the corresponding values at particular wavelengths which correspond to that of the multispectral images. The foreground signals can be computed by subtracting estimated background signals from corresponding input signals. A threshold value can additionally be applied to remove noise variations from the background. Further video analytics, such as region growing, can also be applied to remove spurious, isolated, or small regions.

Another embodiment of the invention may apply an image segmentation technique to segment the multispectral images into high contrast regions, such as sky, building, trees, land, etc. The above foreground and background extraction approach can then be applied to each region. This embodiment yields a more accurate background estimation along the borders of regions.

Figure 2B:
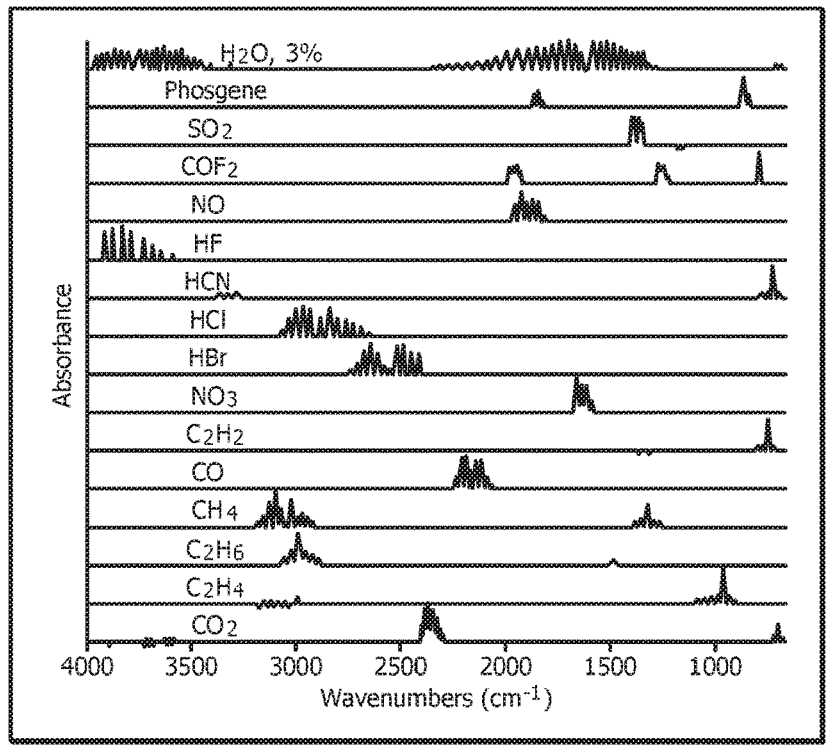

Referring now to FIG. 2B, gas radiance, $R_g$, may be mainly caused by energy exchange (emission or absorption at characteristic spectral bands as shown in FIG. 2B) between the gas and its nearby environment. The gas radiance can be approximated as: $R_g(\lambda)=(1-\tau_g(\lambda))*\delta T*CL*R_B(\lambda)$, where $\tau_g$ is transmittance, $\delta T$ is temperature difference, CL is concentration times path length of the gas cloud, and $R_B$ is the background radiance. The total radiance becomes the sum of the background radiance, gas radiance and its attenuation by the foreground atmosphere.

Figure 2C:
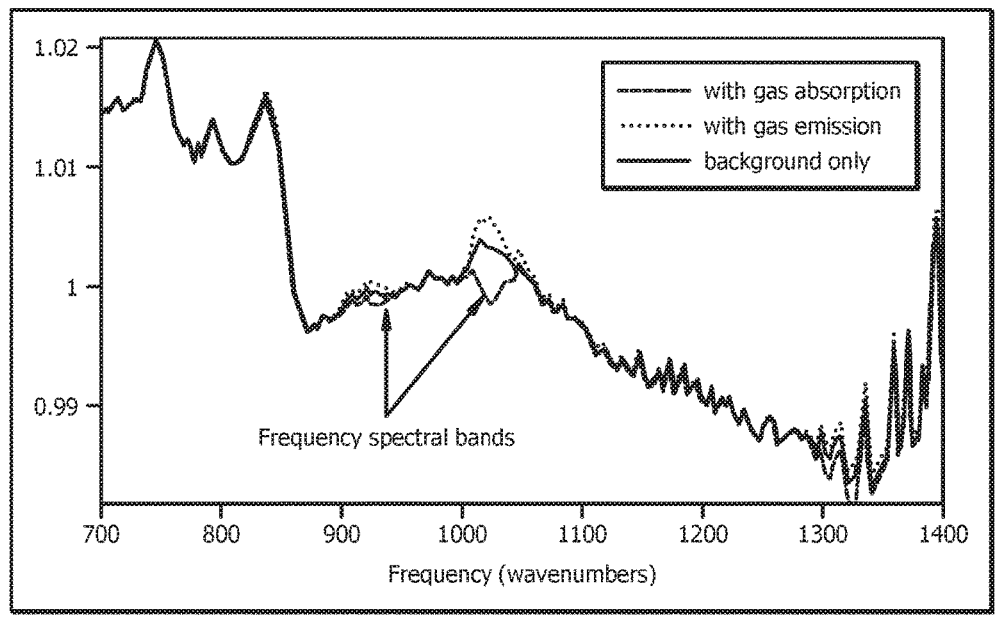

FIG. 2C illustrates that a challenge of gas detection is to remove the background radiance, which is often more than 99% of the total radiance within the characteristic spectral bands.

Conventional gradient-based background removal approaches have been found ineffective in such conditions. By contrast, embodiments disclosed herein apply spectral interpolation to estimate the background radiance. As an example, the background can be assumed to be a black body whose radiance satisfy the Planck's function: $R_{\tilde{B}}(\lambda)=2hc^2/\lambda^5/(\exp(hc/\lambda kT)-1)$, where T is the temperature and $\lambda$ is the wavelength. The background temperature can be estimated based on the best fit using the multi-spectral pixel intensities. The background radiances at the feature spectral bands can then be computed with the estimated temperature. Thus, the background estimation benefits from both the spectral and spatial information.

Figure 2D:
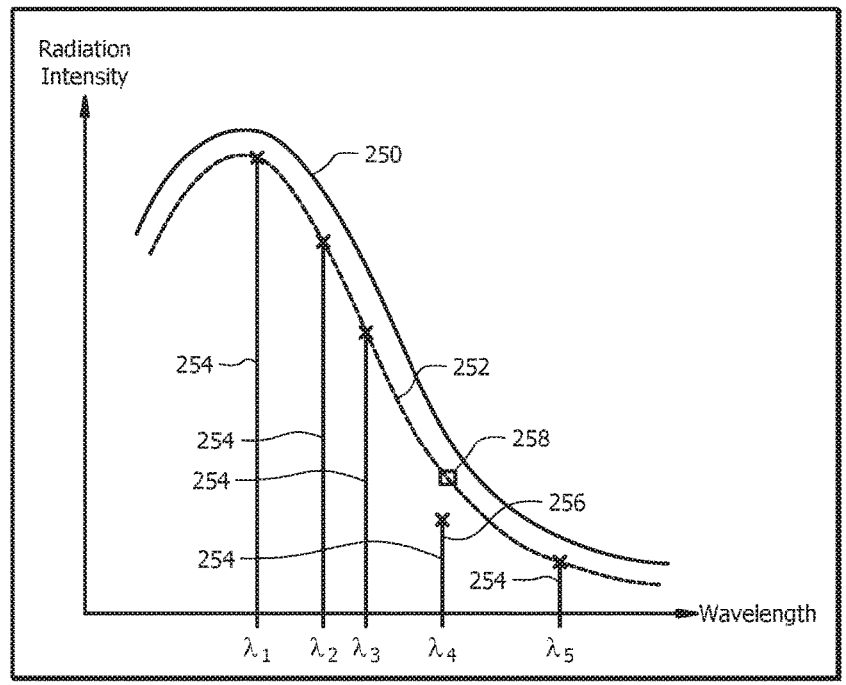

Another embodiment for estimating the background models the background as a gray body, which is parameterized by temperature (T) and emissivity ($\epsilon$) of the background as $R_{\tilde{B}}(\lambda)=2hc^2/\lambda^5/(\exp(hc\epsilon/\lambda kT)-1)$. Both parameters are estimated from the multispectral pixels. FIG. 2D illustrates this process. Multispectral pixels at multiple wavelengths, 254, are the calibrated radiance/intensity measurements from a background region. Using these measurements, an exponential regression may be applied to estimate the temperature and emissivity, and thus the gray body radiation 252. For reference, the black body radiation 250 at the estimated temperature is also shown. Spectral pixel 256 at wavelength $\lambda 4$ represents the calibrated radiance/intensity measurements from the background plus foreground. The background radiation 258 at wavelength $\lambda 4$ may be estimated from the gray body radiation 252. Foreground radiation may then be computed based on the subtraction of background radiation 258 from the total radiation at the spectral pixel 256. FIG. 2D shows estimation of one foreground pixel at one wavelength. Foregrounds at more wavelengths, however, can be estimated.

Figure 3:
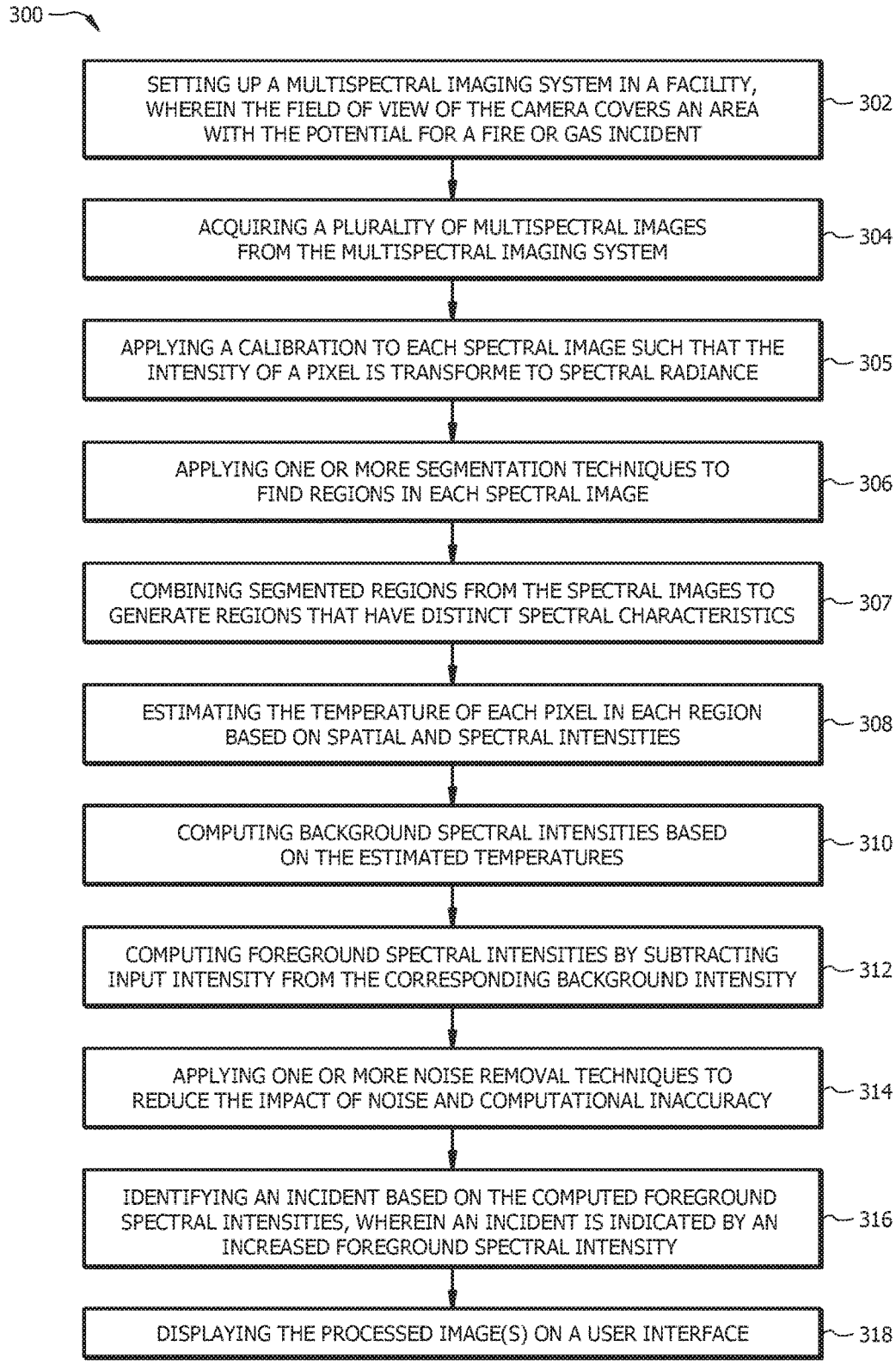
FIG. 3 illustrates a method for detection of background and foreground radiances captured by a multispectral imaging device according to an embodiment of the disclosure.

FIG. 3 illustrates a method 300 for detection of background and foreground radiances captured by a multispectral imaging device. In some embodiments, at least a portion of the method 300 may be completed by a processing device 110 (shown in FIG. 1).

At step 302, a multispectral imaging system (camera) may be set up in a facility wherein the field of view of the camera covers an area with the potential for a fire or gas incident. At step 304, multiple multispectral images may be acquired from a multispectral imaging system (camera), and at step 305, calibration may be applied to each spectral image such that the intensity of a pixel is transformed to spectral radiance. (Intensity and radiance may be used interchangeably.) At step 306, segmentation technique(s) may be applied to find regions in each spectral image. At step 307, segmented regions from all spectral images are combined generating regions that have distinct spectral characteristics. At step 308, the temperature of each pixel may be estimated in each region based on spatial and spectral intensities. Estimation may be based on averaging the temperatures computed from multi-spectral pixel intensities or based on temperature computed from average of multi-spectral pixel intensities. In some embodiments, neighborhood pixel intensities may be used for better fit.

At step 310, background spectral intensities may be computed based on the estimated temperatures. At step 312, the foreground may be computed from subtraction of input intensity from the corresponding background intensity. In some embodiments, at step 314, noise removal technique(s) may be applied to reduce the impact of noise and computational inaccuracy. At step 316, an incident may be identified based on the computed foreground spectral intensities, wherein an incident may be indicated by a change in foreground spectral intensity, which may be an increase or decrease. The increase or decrease in foreground spectral intensity depends on if the gas is absorbing or radiating, which depends on the sign of dT. In some embodiments, the incident play be automatically identified when the computed foreground spectral intensities are higher than a predefined threshold. In some embodiments, at step 318, the processed image(s) may be displayed on a user interface.

Certain risks have been identified in carrying out gas and fire detection according to embodiments set forth herein. For example, the specification of the amount of gas radiance required for gas detection may affect the accuracy of the detection. Four factors can generally affect the gas radiance: $\lambda_g(\lambda)$, $\delta T$, CL and the distance of a gas cloud to the detector. Careful selection of the dominant spectral bands of the target gas can relieve the $\tau_g(\lambda)$ factor. The other three factors depend on operation parameters and can generally not be controllable. Gas cloud radiance on top of the background radiance can be simulated with variations of these factors. Assessment of the detection performance on the simulated data indicates the requirements of these factors. Additionally, the sufficiency of the number of spectral bands for gas detection may affect the accuracy of the detection. Generally, a higher number of narrow spectral bands may be preferred. This can be accomplished by increasing the number of filters on the filter wheel, which may require higher cost and system complexity. Embodiments disclosed herein address performance degradation of using less numbers of spectral bands.

An affordable microbolometer offers additional benefits of localization and visualization of the fire and gas cloud. Accordingly, such embodiments are improvements over existing products and technologies which do not feature a single unit that can perform fire and gas detection as proposed.

Embodiments of the disclosure may be incorporated into a system that has a multispectral imaging device, a memory, a processor, and a user interface. These components can be integrated into a single unit or they may be at different locations connected with communication links. The multispectral imaging device can simultaneously capture images of the scene at different wavelengths.

Alternatively, the multispectral imaging device can sequentially capture images of the scene at different wavelengths in such a short time faster than the motion of the foreground. These captured multispectral images can be saved in the memory and can be accessible by the processor. The separated background and foreground results can then be forwarded to a user interface for viewing. The processor can also use the results in another application, such as identification of the foreground region as a specific gas type.

While various embodiments in accordance with the principles disclosed herein have been shown and described above, modifications thereof may be made by one skilled in the art without departing from the spirit and the teachings of the disclosure. The embodiments described herein are representative only and are not intended to be limiting. Many variations, combinations, and modifications are possible and are within the scope of the disclosure. Alternative embodiments that result from combining, integrating, and/or omitting features of the embodiment(s) are also within the scope of the disclosure. Accordingly, the scope of protection is not limited by the description set out above, but is defined by the claims which follow, that scope including all equivalents of the subject matter of the claims. Each and every claim is incorporated as further disclosure into the specification and the claims are embodiment(s) of the present invention(s).

Furthermore, any advantages and features described above may relate to specific embodiments, but shall not limit the application of such issued claims to processes and structures accomplishing any or all of the above advantages or having any or all of the above features.

Additionally, the section headings used herein are provided for consistency with the suggestions under 37 C.F.R. 1.77 or to otherwise provide organizational cues. These headings shall not limit or characterize the invention(s) set out in any claims that may issue from this disclosure. Specifically and by way of example, although the headings might refer to a "Field," the claims should not be limited by the language chosen under this heading to describe the so-called field. Further, a description of a technology in the "Background" is not to be construed as an admission that certain technology is prior art to any invention(s) in this disclosure. Neither is the "Summary" to be considered as a limiting characterization of the invention(s) set forth in issued claims. Furthermore, any reference in this disclosure to "invention" in the singular should not be used to argue that there is only a single point of novelty in this disclosure. Multiple inventions may be set forth according to the limitations of the multiple claims issuing from this disclosure, and such claims accordingly define the invention(s), and their equivalents, that are protected thereby. In all instances, the scope of the claims shall be considered on their own merits in light of this disclosure, but should not be constrained by the headings set forth herein.

Use of broader terms such as comprises, includes, and having should be understood to provide support for narrower terms such as consisting of, consisting essentially of, and comprised substantially of. Use of the term "optionally," "may," "might," "possibly," and the like with respect to any element of an embodiment means that the element is not required, or alternatively, the element is required, both alternatives being within the scope of the embodiment(s). Also, references to examples are merely provided for illustrative purposes, and are not intended to be exclusive.

While several embodiments have been provided in the present disclosure, it should be understood that the disclosed systems and methods may be embodied in many other specific forms without departing from the spirit or scope of the present disclosure. The present examples are to be considered as illustrative and not restrictive, and the intention is not to be limited to the details given herein. For example, the various elements or components may be combined or integrated in another system or certain features may be omitted or not implemented.

Also, techniques, systems, subsystems, and methods described and illustrated in the various embodiments as discrete or separate may be combined or integrated with other systems, modules, techniques, or methods without departing from the scope of the present disclosure. Other items shown or discussed as directly coupled or communicating with each other may be indirectly coupled or communicating through some interface, device, or intermediate component, whether electrically, mechanically, or otherwise. Other examples of changes, substitutions, and alterations are ascertainable by one skilled in the art and could be made without departing from the spirit and scope disclosed herein.

What is claimed is:

1. A system comprising:
   a multispectral imaging device operable to capture images of a field of view at different wavelengths; and
   an electronic processing device coupled to the multispectral imaging device, wherein the processing device comprises a processor, a memory, and a user interface, and wherein the processing device is operable to:
   save multispectral images to the memory for access by the processor;
   apply one or more segmentation techniques to find regions in each multispectral image;
   combine segmented regions from the multispectral images to generate regions that have distinct spectral characteristics;
   estimate background parameters of each pixel in each region based on spatial and spectral intensities;
   compute background spectral intensities based on the estimated background parameters;
   compute foreground spectral intensities by subtracting input intensity from the corresponding background intensity; and
   identify an incident based on the computed foreground spectral intensities, wherein an incident is indicated by a change in foreground spectral intensity; and
   generate an alarm when a foreground region indicates a hazardous incident.

2. The system of claim 1, wherein the multispectral imaging device comprises a microbolometer.

3. The system of claim 1, wherein the electronic processing device is incorporated into the multispectral imaging device.

4. The system of claim 1, wherein the multispectral imaging device comprises a filter wheel operable to filter different wavelengths as it rotates in front of a camera.

5. The system of claim 1, wherein the multispectral imaging device comprises a lens array that is split into different wavelengths.

6. The system of claim 1, wherein the multispectral imaging device comprises a plurality of cameras located within the multispectral imaging device.

7. The system of claim 1, wherein the incident comprises a gas leak.

8. The system of claim 7, wherein the processing device is operable to identify a specific gas type, and wherein the alarm is generated if the gas is identified to be a hazardous gas.

9. The system of claim 1, wherein the incident comprises a fire.

10. A method for detection of background and foreground radiances captured by a multispectral imaging device, the method comprising:
    acquiring a plurality of spectral images from a multispectral imaging system in a facility, wherein a field of view of the multispectral imaging system covers an area with a potential for a fire or gas incident;
    applying a calibration to each spectral image of the plurality of spectral images such that an intensity of a pixel is transformed to a spectral radiance;
    applying one or more segmentation techniques to find segmented regions in each of the spectral images;
    combining the segmented regions from the spectral images to generate regions that have distinct spectral characteristics;
    estimating background parameters of each pixel in each region based on spatial and spectral intensities;
    computing background spectral intensities based on the estimated background parameters;
    computing foreground spectral intensities by subtracting input intensity from the corresponding background intensity; and identifying an incident based on the computed foreground spectral intensities, wherein an incident is indicated by a change in foreground spectral intensity.

11. The method of claim 10, wherein the incident is identified when the computed foreground spectral intensities are higher or lower than predefined thresholds.

12. The method of claim 10, further comprising displaying the processed images on a user interface.

13. The method of claim 10, wherein estimation is based on averaging the background parameters computed from multi-spectral pixel intensities.

14. The method of claim 10, wherein the background parameters include temperature and emissivity.

15. The method of claim 10, further comprising applying one or more noise removal techniques to reduce the impact of noise and computational inaccuracy.

16. A system comprising:
a multispectral imaging device operable to capture images of a location at different wavelengths; and
an electronic processing device coupled to the multispectral imaging device, wherein the processing device comprises a processor, a memory, and a user interface, and wherein the processing device is operable to:
acquire a plurality of spectral images from the multispectral imaging device;
apply a calibration to each spectral image such that the intensity of a pixel is transformed to spectral radiance;
apply one or more segmentation techniques to find regions in each spectral image;
combine segmented regions from the spectral images to generate regions that have distinct spectral characteristics;
estimate the background parameters, including temperature and emissivity, of each pixel in each region based on spatial and spectral intensities;
compute background spectral intensities based on the estimated background parameters;
compute foreground spectral intensities by subtracting input intensity from the corresponding background intensity; and
identify an incident based on the computed foreground spectral intensities, wherein an incident is indicated by a change in foreground spectral intensity.

17. The system of claim 16, wherein the multispectral imaging device comprises a microbolometer.

18. The system of claim 16, wherein the incident is identified when the computed foreground spectral intensities are higher or lower than predefined thresholds.

19. The system of claim 16, wherein the processing device is further operable to display the processed images on a user interface.

20. The system of claim 16, wherein the processing device is operable to apply one or more noise removal techniques to reduce the impact of noise and computational inaccuracy.

* * * * *